US00PP37782P3

(12) United States Plant Patent
Bull

(10) Patent No.: US PP37,782 P3
(45) Date of Patent: Oct. 13, 2026

(54) ***ECHINACEA* PLANT NAMED 'BullEchipur 117'**

(50) Latin Name: *Echinacea purpurea*
Varietal Denomination: BullEchipur 117

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 92 days.

(21) Appl. No.: 18/536,997

(22) Filed: Dec. 12, 2023

(65) Prior Publication Data

US 2025/0185556 A1 Jun. 12, 2025

(51) Int. Cl.
*A01H 5/02* (2018.01)
*A01H 6/14* (2018.01)

(52) U.S. Cl.
USPC ..... Plt./428
CPC ..... *A01H 6/1448* (2018.05); *A01H 5/02* (2013.01)

(58) Field of Classification Search
USPC ..... Plt./428
CPC ..... A01H 5/02; A01H 5/00; A01H 6/1448; A01H 6/14
See application file for complete search history.

(56) References Cited

PUBLICATIONS

Nursery Guide for *Echinacea* Vintage Yellow, retrieved on Jul. 14, 2025 at https://nurseryguide.com/find_plants/echinacea-hybrida-vintage-yellow, one page. (Year: 2025).*
Premier Color Nursery, Inc. Week 36 Availability 2023, retrieved on Dec. 8, 2025 at https://static1.squarespace.com/static/62b21fbd0748d162770ccbad/t/64f100d0ae7ffd36540c827f/1693515985092/2023-Availability+Week+36.pdf, pp. 1-6 (Year: 2023).*

* cited by examiner

*Primary Examiner* — June Hwu
(74) *Attorney, Agent, or Firm* — The Webb Law Firm

(57) ABSTRACT

A new and distinct variety of *Echinacea* plant having a very compact growth habit and numerous, yellow colored blooms.

1 Drawing Sheet

Botanical classification: *Echinacea purpurea.*
Varietal denomination: 'BullEchipur 117'.

BACKGROUND OF THE INVENTION

The present invention comprises a new and distinct cultivar of *Echinacea* plant known by the varietal name 'BullEchipur 117'. The new variety was discovered in August of 2020 in Gönnebek, Germany as the result of a planned breeding program with the purposes of providing *Echinacea* plants with yellow colored flowers, as well as a more compact growth habit, more uniformity, good branching, early flowering, and good propagation when compared to prior *Echinacea* plants known to the breeder. The new variety is the result of a cross between an unpatented *Echinacea purpurea* variety having an internal breeder's reference of "BUL 2018-36" (female parent) and an unpatented *Echinacea purpurea* variety having an internal breeder's reference of "BUL 2018-28" (male parent) from the breeder's own collection. The new variety was first asexually reproduced via in-vitro tissue culture cuttings in Gönnebek, Germany in September of 2020. The new variety is similar to its parental varieties in botanical classification, but exhibits a different flower color, more compact growth habit, and smaller leaves than both of its parental varieties. 'BullEchipur 117' also has better branching and a shorter height than its female parent. Further, the new variety produces more flowers with earlier flowering than its male parent.

When 'BullEchipur 117' is compared to *Echinacea purpurea* variety named 'Cheyenne Spirit' (unpatented), 'BullEchipur 117' is similar to 'Cheyenne Spirit' in botanical classification and yellow flower color, but the new variety exhibits more compact, shorter growth with increased branching, more flowers per plant that are also of a uniform yellow color, and more healthy, smaller leaves that distinguish it from 'Cheyenne Spirit'. Further, the following characteristics distinguish 'BullEchipur 117' when generally compared to other *Echinacea* varieties known to the breeder:

Very compact growth habit;
Yellow flower color;
High flower number per plant;
High branching;
A uniform growth habit;
Smaller leaves; and
A fast crop time.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWING

The accompanying photographic drawing illustrates the new variety at 23 weeks of age, with the color being as nearly true as is possible with color illustrations of this type.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 19 cm (3 liter) pots under normal field production conditions, and the color readings and measurements were observed outdoors under natural light on 23 week old plants in Gönnebek, Germany. Color references are primarily to The 2015 R.H.S. Colour Chart of The Royal Horticultural Society of London, Sixth Edition, except where terms of ordinary significance are used.

PLANT

Time to initiate roots: About 7 days at approximately 19-20° C.

Time to develop roots: About 40-50 days at approximately 18° C.

Time to produce a finished flowering plant from a rooted cutting: About 12-14 weeks in a 19 cm container.

Rooting habit: Exhibits numerous roots that are freely branching and healthy in appearance.

Plant height: 30.0-40.0 cm.

Plant width: 30.0-35.0 cm.

Habit: Upright, very compact growth with numerous branches.

Disease/pest resistance: Nothing unusual noted to date.

Temperature tolerance: Nothing unusual noted to date.

Drought tolerance: Average.

Branches (flowering stems):

*Number per plant.*—20-28.
*Length.*—20.0-25.0 cm.
*Diameter.*—3.0-8.0 mm.
*Internode length.*—1.0-4.0 cm.
*Angle.*—Upright and outward.
*Strength.*—Strong.
*Texture.*—Pubescence present.
*Color.*—Close to Yellow-Green Group RHS 146C.

Foliage:

*Arrangement.*—Single.
*Leaf.*—Length: 10.0-12.0 cm on average. Width: 1.0-5.0 cm. Shape: Lanceolate. Apex: Acuminate. Base: Attenuate to acute. Margin: Entire. Aspect: Straight to curved. Texture: Upper surface: Rough. Lower surface: Rough. Color: Young leaves: Upper surface: Close to Green Group RHS 137A. Lower surface: Close to Green Group RHS 137C. Mature leaves: Upper surface: Close to Green Group RHS 137A. Lower surface: Close to Green Group RHS 137C. Petiole: None present. Veins: Venation type: Cross-venulate to longitudinal. Color: Upper surface: Close to Yellow-Green Group RHS 145A. Lower surface: Close to Yellow-Green Group RHS 145B.

INFLORESCENCE

Bud:

*Diameter.*—1.0-3.0 cm.
*Length.*—1.2-2.0 cm.
*Color.*—Close to Green Group RHS NN137C.

Appearance: Elliptic-shaped ray florets and tubular-shaped disc florets.

Natural flowering season: Flowering occurs from July-September in Gönnebek, Germany, beginning approximately 12-14 weeks after planting.

Average number of inflorescences per plant: 20-30.

Average number of inflorescences per branch: 1-3.

Disc and ray floret arrangement: Disc florets are arranged in the middle of the receptacle of the composite, single, freely flowering plant, with ray florets extending outwardly therefrom.

Fragrance: None.

Inflorescence:

*Diameter.*—4.0-10.0 cm.
*Height (depth).*—2.0-4.0 cm.
*Diameter of disc.*—1.5-4.0 cm.
*Receptacle height.*—1.0 cm.
*Receptacle diameter.*—1.5-4.0 cm.

Ray florets:

*Number per inflorescence.*—15-24.
*Arrangement.*—In two or three whorls.
*Attitude.*—Semi-drooping.
*Predominate type.*—Ligulate (flat).
*Profile in cross section.*—Flat to weakly concave.
*Length.*—1.6-3.5 cm.
*Width.*—0.9-1.5 cm.
*Shape.*—Elliptical.
*Apex.*—Mix of Obtuse to Acute.
*Apex notch.*—Shallow.
*Base.*—Acute.
*Margin.*—Entire.
*Texture.*—Upper surface: Smooth and glabrous. Lower surface: Rough.
*Color.*—When opening: Upper surface: Close to Yellow-Orange Group RHS 21B. Lower surface: Close to Yellow-Orange Group RHS 16C. At maturity: Upper surface: Close to Yellow-Orange Group RHS 17C. Lower surface: Close to Yellow-Orange Group RHS 16C. Ground color description: Close to Yellow-Orange Group RHS 17C.
*Venation.*—Appearance: Parallel. Color: Upper surface: Same color as the florets. Lower surface: Same color as the florets.

Disc florets:

*Number per inflorescence.*—Approximately 200-400.
*Arrangement.*—In the center of receptacle.
*Diameter in relation to the flower head.*—Medium to large.
*Length.*—8.0-15.0 mm.
*Width.*—1.0-2.0 mm.
*Shape.*—Tubular.
*Apex.*—Pointed.
*Color.*—Immature: Close to Yellow-Orange Group RHS 22A. At maturity: Close to Yellow-Orange Group RHS 22A.

Phyllaries:

*Number per inflorescence.*—40-55.
*Arrangement.*—In 3-4 whorls.
*Length.*—Approximately 0.5-1.0 cm.
*Width.*—2.0-4.0 mm.
*Shape.*—Lanceolate.
*Apex.*—Elongated oval.
*Base.*—Fused.
*Margin.*—Entire.
*Texture.*—Upper surface: Rough. Lower surface: Rough.
*Color.*—Immature: Upper surface: Close to Green Group RHS NN137C. Lower surface: Close to Green Group RHS NN137C. At maturity: Upper surface: Close to Green Group RHS NN137C. Lower surface: Close to Green Group RHS NN137C.

Reproductive organs:

Androecium:

*Presence*.—On disc florets.

*Number* (*per floret*).—One.

*Filament length*.—1.0-2.0 mm.

*Filament color*.—Close to Green-Yellow Group RHS 1B.

*Anther*.—Shape: Oval. Length: 1.0 mm. Color: Close to Greyed-Purple Group RHS 183B.

*Pollen*.—Color: Close to Yellow-Orange Group RHS 15B. Amount: Plentiful; too difficult to quantify.

Gynoecium:

*Presence*.—In disc and ray florets.

*Pistil length*.—1.0-2.0 mm.

*Stigma*.—Shape: Two-parted. Color: Close to Green-Yellow Group RHS 1B.

*Style*.—Length: 1.0-2.0 mm. Color: Close to Greyed-Purple Group RHS 187B. Seeds:

*Overall size*.—1.0-2.0 mm.

Receptacle spine:

*Number per inflorescence*.—Approximately 200-400.

*Type*.—Hypogynous receptacle.

*Length*.—10-12 mm.

*Color*.—23A.

I claim:

1. A new and distinct variety of *Echinacea* plant named 'BullEchipur 117', as is herein illustrated and described.

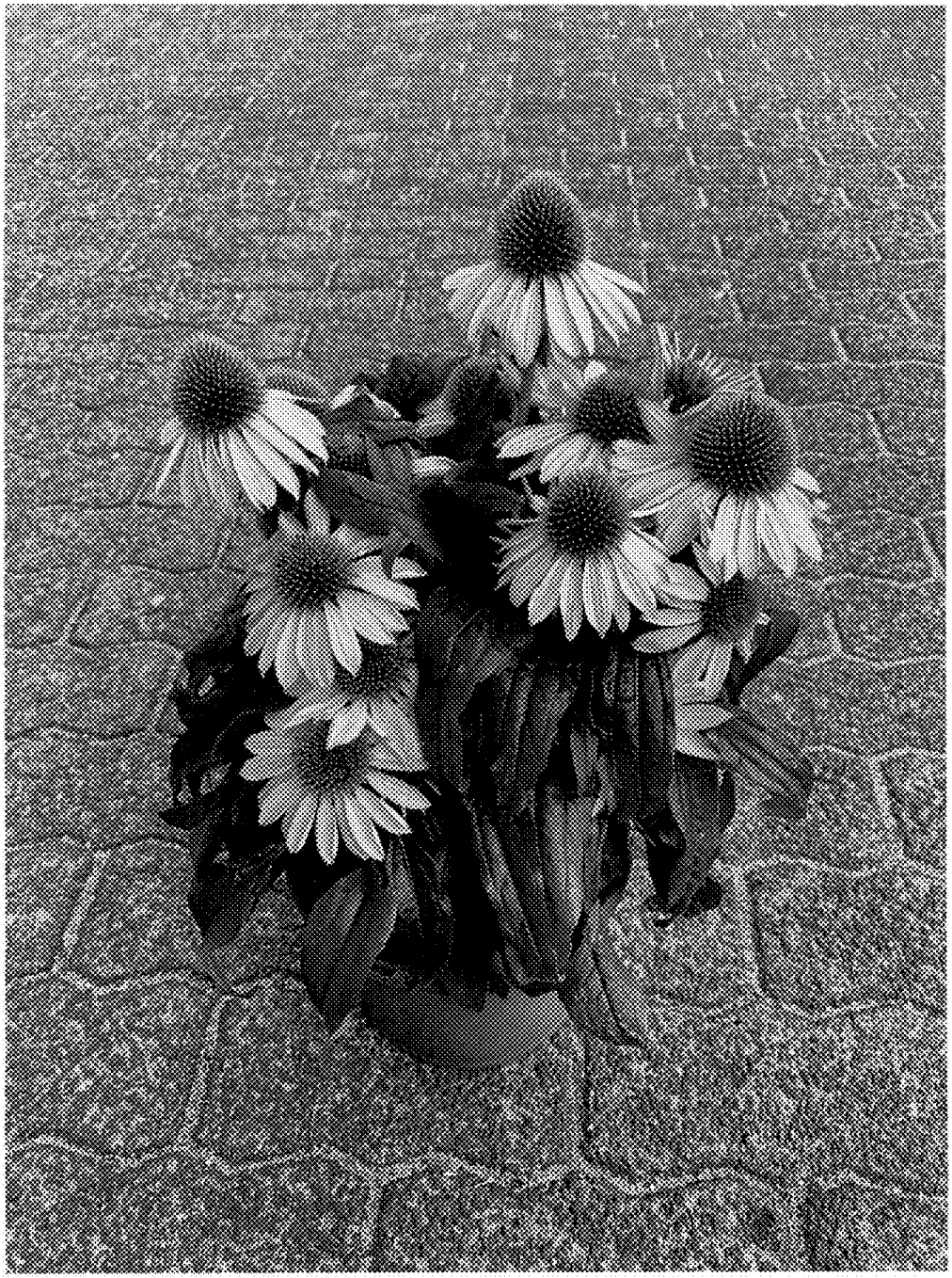

* * * * *